(12) United States Patent
Nakatani et al.

(10) Patent No.: US 8,966,960 B2
(45) Date of Patent: Mar. 3, 2015

(54) MEASURING DEVICE

(75) Inventors: Masaya Nakatani, Hyogo (JP); Makoto Takahashi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 361 days.

(21) Appl. No.: 13/636,926

(22) PCT Filed: Apr. 19, 2011

(86) PCT No.: PCT/JP2011/002273
§ 371 (c)(1),
(2), (4) Date: Sep. 24, 2012

(87) PCT Pub. No.: WO2011/135802
PCT Pub. Date: Nov. 3, 2011

(65) Prior Publication Data
US 2013/0015065 A1 Jan. 17, 2013

(30) Foreign Application Priority Data

Apr. 27, 2010 (JP) ................. 2010-101731

(51) Int. Cl.
*G01N 29/00* (2006.01)
*G01N 33/487* (2006.01)
*G01N 29/02* (2006.01)

(52) U.S. Cl.
CPC ........ *G01N 33/48728* (2013.01); *G01N 29/022* (2013.01)
USPC ....................................... 73/64.53

(58) Field of Classification Search
CPC .. G01N 29/022; G01N 29/222; G01N 29/036
USPC ......................................... 73/64.53
See application file for complete search history.

(56) References Cited

U.S. PATENT DOCUMENTS 7,846,389 B2 * 12/2010 Owen et al. ................ 422/82.01
8,058,056 B2 * 11/2011 Lee et al. .................... 435/288.5
(Continued)

FOREIGN PATENT DOCUMENTS

JP      2008-000079      1/2008
WO   WO-2005/089253 A2   9/2005
(Continued)

OTHER PUBLICATIONS

J.J. Hawkes et al., "Ultrasonic deposition of cells on a surface," Biosensors and Bioelectronics 19 (2004) 1021-1028.
(Continued)

*Primary Examiner* — Hezron E Williams
*Assistant Examiner* — Rodney T Frank
(74) *Attorney, Agent, or Firm* — McDermott Will & Emery LLP

(57) ABSTRACT

A measuring device is configured to measure a reaction of test objects suspended in a first liquid. The measuring device includes a base and a vibration generator. The base has a first cavity and second cavities provided therein. The first cavity is configured to store the first liquid. The vibration generator generates a standing wave in the first liquid stored in the first cavity. The base has through-holes provided therein. Each of the through-holes allows respective one of the second cavities to communicate with the first cavity. The through-holes have opening sections. The opening sections open to the first cavity and are configured to capture the test objects. This measuring device can measure a test objects with a high efficiency.

10 Claims, 10 Drawing Sheets

(56) References Cited

U.S. PATENT DOCUMENTS

| | | |
|---|---|---|
| 2003/0180965 A1* | 9/2003 | Yobas et al. .................. 436/180 |
| 2007/0155016 A1 | 7/2007 | Lee et al. |
| 2010/0000650 A1 | 1/2010 | Matthiesen et al. |
| 2010/0015008 A1 | 1/2010 | Ong et al. |
| 2010/0055673 A1 | 3/2010 | Agarwal et al. |
| 2010/0126922 A1 | 5/2010 | Takahashi et al. |

FOREIGN PATENT DOCUMENTS

| | | |
|---|---|---|
| WO | WO-2007/108779 A1 | 9/2007 |
| WO | WO-2007/139511 A1 | 12/2007 |
| WO | WO-2008/142850 | 11/2008 |

OTHER PUBLICATIONS

S.P. Martin et al., "Spore and micrp-particle capture on an immunosensor surface in an ultrasonic standing wave system," Biosensors and Bioelectronics 21 (2005) 758-767.

L.A. Kuznetsova et al., "Applications of ultrasound streaming and radiation force in biosensors," Biosensors and Bioelectronics 22 (2007) 1567-1577.

T. Laurell et al., "Chip integrated strategies for acoustic separation and manipulation of cells and particles," Chemical Society Reviews, The Royal Society of Chemistry 2007.

International Search Report issued in International Patent Application No. PCT/JP2011/002273 dated Jul. 19, 2011.

* cited by examiner

MEASURING DEVICE

This application is the U.S. National Phase under 35 U.S.C. §371 of International Application No. PCT/JP2011/002273, filed on Apr. 19, 2011, which in turn claims the benefit of Japanese Application No. 2010-101731, filed on Apr. 27, 2010, the disclosures of which Applications are incorporated by reference herein.

TECHNICAL FIELD

The present invention relates to a measuring device for measuring the property of a test object, such as a cell or tissue-derived film. The present invention also relates to a measuring device for measuring the status of a particulate matter existing in liquid.

BACKGROUND ART

FIG. 8 is a cross-sectional view of conventional measuring device 501. Measuring device 501 is a cellular electrophysiology sensor. Measuring device 501 includes substrate 1 having partition wall section 3. Substrate 1 has cavities 2 and 5 provided therein. Cavity 5 communicates with cavity 2 via through-hole 4 provided in partition wall section 3.

Cavities 2 and 5 are filled with measuring solution of electrolytic solutions. Then, cell 6, a test object, is injected to cavity 2. When the electrolytic solution is sucked from cavity 5, cell 6 can be captured at opening section of through-hole 4 near cavity 2.

While cell 6 is captured, agent is injected to cavity 2 to measure a potential difference between the electrolytic solutions in cavities 2 and 5 and the current flowing between cavities 2 and 5. Depending on the measured potential difference or current value, a potential change and a current value change at the interior or exterior of cell 6 during the activity of the cell as well as a physicochemical change caused by the activity of the cell can be measured.

Measuring devices similar to conventional measuring device 501 are disclosed in Patent Publication 1 and Patent Publication 2.

In conventional measuring device 501, a deteriorated measuring efficiency may be caused by a defective adhesion or a failed suction of the test object or a loss in the time to inject the measuring solution or agent for example. When cell 6 is measured as a test object in particular, one cell 6 is required to contact one through-hole 4 securely. Generally, an electrophysiological reaction generated by cell 6 (e.g., a potential difference generated at the interior or exterior of the cell or the value of the current flowing the interior or exterior of the cell) is a very small reaction. If cell 6 insufficiently contacts through-hole 4 and produces a gap between cell 6 and partition wall section 3, an electrical leak is caused via the gap. This electrical leak prevents an accurate measuring of the electrophysiological reaction at the interior or exterior of the cell.

In the case that cell 6 is subjected to the defective adhesion as described above, noise caused by the electrical leak prevents the measurement from being carried out accurately, thus failing to provide measuring data. Thus, another measuring device is newly prepared and used to perform the measurement from scratch, thereby causing the measuring of the cell electrophysiological reaction less efficiency.

Furthermore, a deteriorated measuring efficiency is also caused by a solid matter other than the test object (e.g., inactivated cells existing in the measuring solution, dusts other than the cell). Specifically, the solid matter existing in the measuring solution may include not only cell 6 as a test object to be measured but also inactivated cells or dust. Thus, if the inactivated cells or dusts are adsorbed by through-hole 4, measuring data cannot be obtained, thus requiring a measurement to be performed from scratch using a separately-prepared measuring device. This consequently causes the measuring of the cell electrophysiological reaction to have a very low efficiency.

CITATION LIST

Patent Literature

Patent literature 1: WO2007/108779
Patent literature 2: WO2007/139511

SUMMARY OF THE INVENTION

A measuring device is configured to measure a reaction of test objects suspended in a first liquid. The measuring device includes a base and a vibration generator. The base has a first cavity and second cavities provided therein. The first cavity is configured to store the first liquid. The vibration generator generates a standing wave in the first liquid stored in the first cavity. The base has through-holes provided therein. Each of the through-holes allows respective one of the second cavities to communicate with the first cavity. The through-holes have opening sections. The opening sections open to the first cavity and are configured to capture the test objects.

This measuring device can measure a test objects with a high efficiency.

DETAIL DESCRIPTION OF PREFERRED EMBODIMENTS

Figure 1:
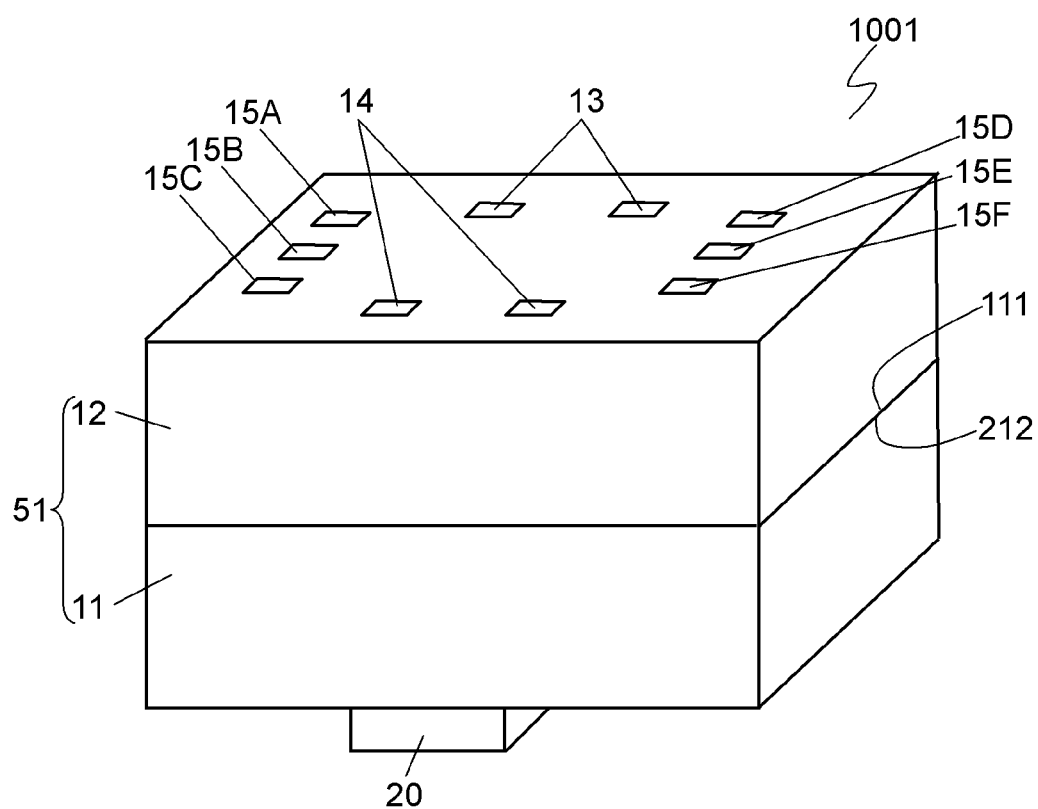
FIG. 1 is a top perspective view of a measuring device in accordance with an exemplary embodiment of the present invention.
Figure 2:
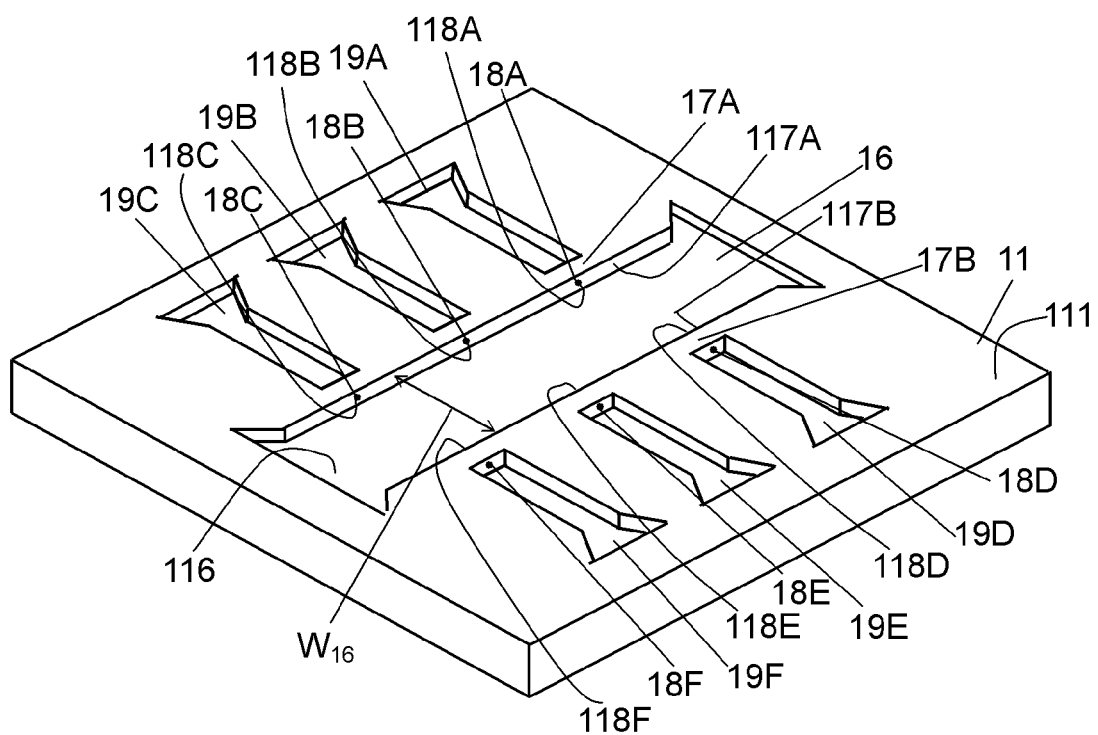
FIG. 2 is a top perspective view of a substrate of the measuring device in accordance with the embodiment.
Figure 3:
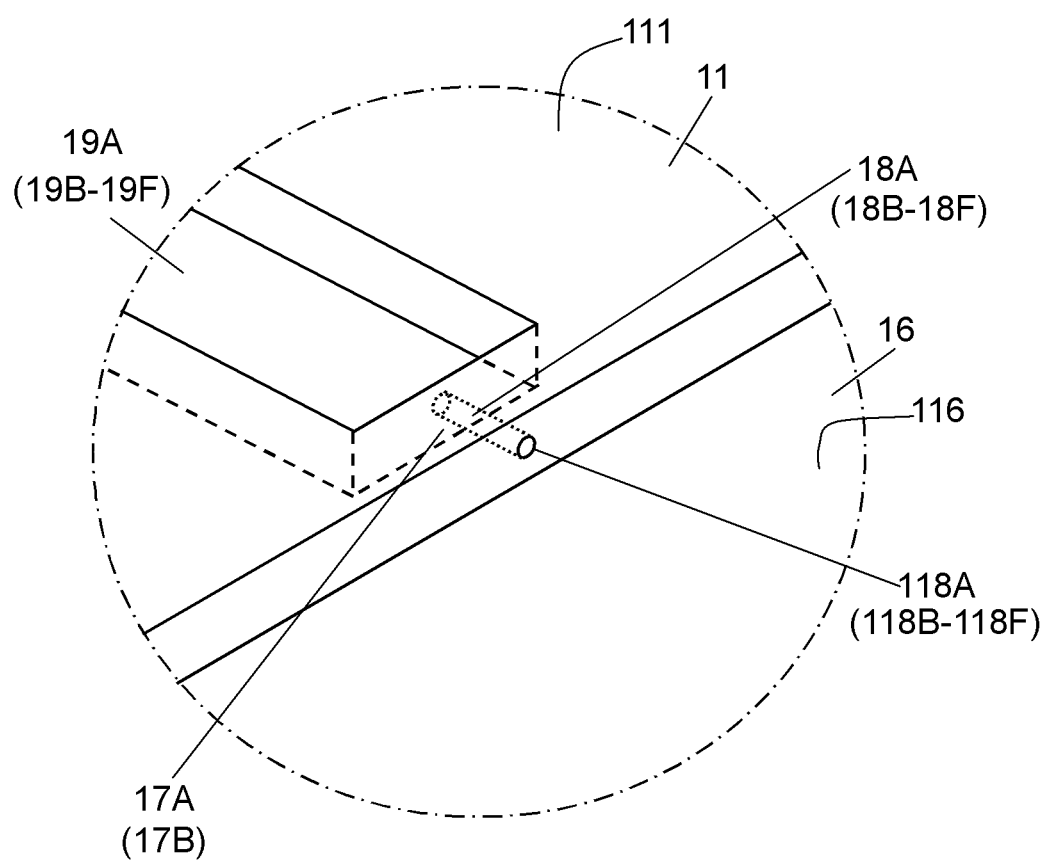
FIG. 3 is an expanded perspective view of the substrate shown in FIG. 2.

FIG. 1 is a top perspective view of measuring device 1001 in accordance with an exemplary embodiment of the present invention. FIG. 2 is a top perspective view of substrate 11 of measuring device 1001. FIG. 3 is an expanded perspective view of measuring device 1001 shown in FIG. 2. Measuring device 1001 includes substrate 11 and substrate 12 joined to upper surface 111 of substrate 11. Substrates 11 and 12 constitute base 51. Two (plural) inlets 13, two (plural) outlets 14, and plural communication openings 15A to 15F are provided in substrate 12. Cavities 16 and 19A to 19F are provided in upper surface 111 of substrate 11. Two inlets 13 and outlets 14 communicate with cavity 16, thus communicating with one another via cavity 16. Liquid, such as solution or chemical solution, entering through inlet 13 flows to outlet 14 through cavity 16. Substrate 11 has partition wall section 17A and partition wall section 17B. Partition wall section 17A is provided between cavity 16 and each of cavities 19A to 19C. Partition wall section 17B is provided between cavity 16 and each of cavities 19D to 19F. Partition wall sections 17A and 17B face each other across cavity 16 and constitute side surfaces 117A and 117B of cavity 16 facing each other. Cavity 16 has bottom surface 116 connected to side surfaces 117A and 117B. Through-holes 18A to 18F are provided in partition wall sections 17A and 17B. Through-holes 18A to 18C have opening sections 118A to 118C opening to side surface 117A, respectively. Through-holes 18D to 18F have opening sections 118D to 118F opening to side surface 117B, respectively. Test objects, solid components, such as cells or tissue-derived films, are captured at opening sections 118A to 118F in cavity 16. Through-holes 18A to 18F are independently connected to cavities 19A to 19F, respectively. Cavities 19A to 19F are independently connected to communication openings 15A to 15F formed in substrate 12, respectively, and are independently connected via communication openings 15A to 15F to an outside of substrates 11 and 12, i.e., base 51, respectively.

Vibration generator 20 is provided on side surfaces 117A and 117B of cavity 16 or a surface of substrate 11 opposite to bottom surface 116 to generate a vibration, such as ultrasonic waves, in substrate 11. The vibration by vibration generator 20 can be used to generate standing waves between side surfaces 117A and 117B in cavity 16. Vibration generator 20 can be a vibration actuator. Vibration generator 20 can be provided at such a position that can provide an efficient generation of standing waves in cavity 16. In order to generate standing waves, width $W_{16}$ of cavity 16, vibration frequency $f_{20}$, and sound velocity $v_{16}$ at which the vibration propagates through the liquid existing in cavity 16 satisfy the following relation.

$$f_{20}=(n/2) \times v_{16}/W_{16}\ (n \text{ is a natural number})$$

When cavity 16 is irradiated with an acoustic wave having frequency $f_{20}$ satisfying the above relation, the acoustic wave is repeatedly reflected in cavity 16 and generate standing waves in an inside of cavity 16. Upon satisfying the above relation, the standing waves have nodes and antinodes depending on the order. Thus, the test objects, solid components, concentrate at the nodes of the standing waves. For example, in the case that cavity 16 has a width (width $W_{16}$) of 200 μm between side surfaces 117A and 117B and vibration generator 20 generates a vibration having a frequency of about 3.5 MHz, then the nodes of the standing waves are formed at the center between side surfaces 117A and 117B of cavity 16. This causes the test objects to concentrate at the center. As described above, the test objects concentrate at a fixed distance from side surfaces 117A and 117B, i.e., opening sections 118A to 118F of through-holes 18A to 18F. When the liquid in cavity 16 is sucked from cavities 19A to 19F, the test objects are sucked with a fixed pressure toward opening sections 118A to 118F of through-holes 18A to 18F. As a result, upon reaching opening sections 118A to 118F, the test objects contact opening sections 118A to 118F of side surfaces 117A and 117B at a constant speed.

When measuring device 1001 is used, cavities 16 and 19A to 19F contain conductive liquid, such as electrolytic solution, therein. The test objects captured at opening sections 118A to 118F adheres to opening sections 118A to 118F to block opening sections 118A to 118F. This provides a giga-seal in which the electrical resistance between the liquid in each of cavities 19A to 19F and the liquid in cavity 16 has a very high value more than 1 GΩ.

The test objects contacting opening sections 118A to 118F at a constant speed improve measuring efficiency. If the test objects contact opening sections 118A to 118F at different speeds, test objects contacting opening sections 118A to 118F at a high speed may be broken by a high impact, thus preventing a subsequent measuring. Test objects contacting opening sections 118A to 118F at a low speed, on the other hand, is insufficiently sucked and is not adhered securely to opening sections 118A to 118F, thus preventing the giga-seal.

Figure 8:
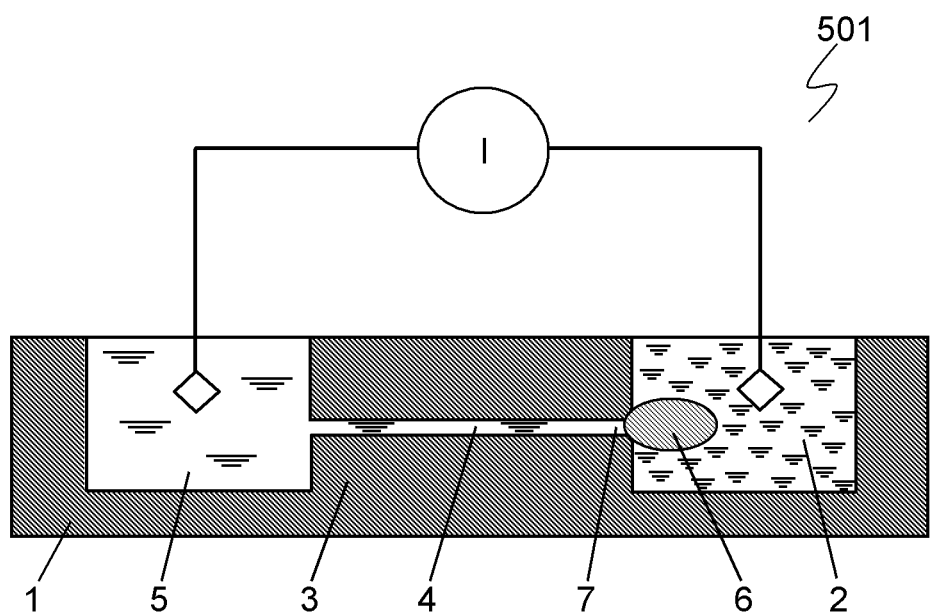
FIG. 8 is a cross-sectional view of a conventional measuring device.

In conventional measuring device 501 shown in FIG. 8, when cell 6, a test object, existing around through-hole 4 is sucked, cell 6 contacts opening section 7 of through-hole 4 at a low speed. This often results in a phenomenon in which cell 6 cannot adhere to opening section 7, thus failing to form a giga-seal.

In measuring device 1001 according to the embodiment, the test objects do not exist around opening sections 118A to 118F of through-holes 18A to 18F. Thus, the test objects are sucked at a constant distance from through-holes 18A to 18F. This consequently reduces the phenomena producing the defective giga-seal due to a low speed. For example, cells generally have a diameter ranging from 10 μm to 20 μm. When test objects are the cells, the standing waves cause the cells to exist at positions away from side surfaces 117A and 117B by a distance not smaller than 30 μm. This distance not smaller than 30 μm prevents the test objects from contacting opening sections 118A to 118F of through-holes 18A to 18F. Then, these cells can be sucked and a contact opening sections 118A to 118F, thus reducing the probability at which a defective giga-seal due to an insufficient speed is caused. In measuring device 1001, test objects are captured at opening sections 118A to 118F by being sucked from positions of a constant distance. Thus, by being sucked by the same suction force, the test objects are stably captured at opening sections 118A to 118F in the same direction and at the same speed.

Partition wall section 17A separates each of cavities 19A to 19C from cavity 16. Partition wall section 17B separates each of cavities 19D to 19F from cavity 16. Each of cavities 19A to 19F communicates with cavity 16 only via respective one of through-holes 18A to 18F provided in partition wall sections 17A and 17B. Each of cavities 19A to 19F communicates to cavity 16 only via respective one of through-holes 18A to 18F independently from each other.

Figure 4:
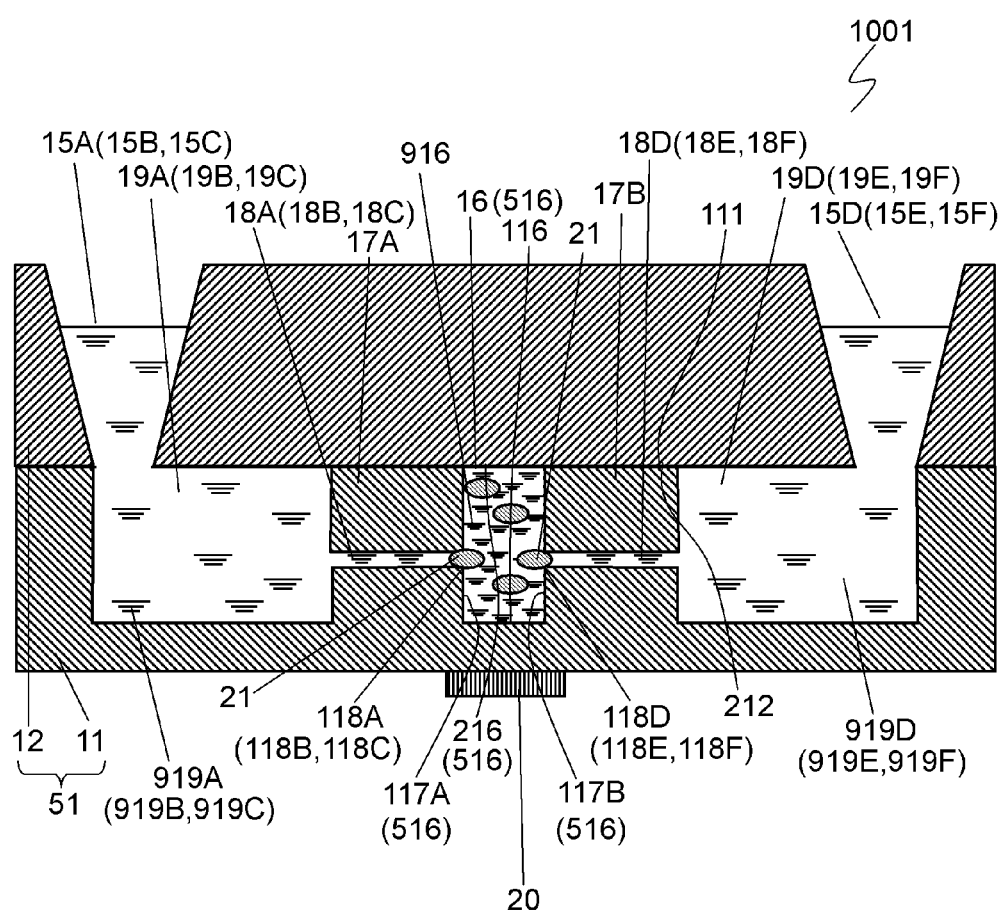
FIG. 4 is a cross-sectional view of the measuring device in accordance with the embodiment.

FIG. 4 is a cross-sectional view of measuring device 1001. As shown in FIG. 4, cavity 16 is surrounded by inner wall surface 516. Inner wall surface 516 of cavity 16 has side surfaces 117A and 117B, bottom surface 116, and upper surface 216 facing bottom surface 116. Cavity 16 is covered up with lower surface 212 of substrate 12. Upper surface 216 is a part of lower surface 212. Opening sections 118A to 118F of through-holes 18A to 18F are provided at positions locating test objects 21 captured at opening sections 118A to 118F away from bottom surface 116 and upper surface 216 of cavity 16 while contacting none of bottom surface 116 and upper surface 216. For example, in the case that test object 21 is a cell having a diameter raging from about 10 to 20 μm, opening sections 118A to 118F are provided preferably at positions locating test objects 21 away from bottom surface 116 and upper surface 216 of cavity 16 by a distance larger than the diameter of test objects 21.

Test objects 21 are captured at opening sections 118A to 118F of through-holes 18A to 18F in cavity 16. Opening sections 118A to 118F have a diameter smaller than the diameter of test objects 21. In the case that test object 21 is a cell having a diameter ranging from about 10 to 20 μm, opening sections 118A to 118F preferably have a diameter ranging from 0.5 μm to 5.0 μm. Opening sections 118A to 118F of through-holes 18A to 18F have a position, a length, and a diameter that can be appropriately changed depending on test object 21 to be measured.

In measuring device 1001 according to the embodiment, substrate 11 can be made of silicon, quartz, or glass.

Substrate 12 may be made of silicon resin, such as polydimethylsiloxane (PDMS) resin, glass, silicon, or quartz. The PDMS resin in particular can robustly adhere to material, such as silicon, quartz, or glass, of substrate 11 without using adhesive agent since the PDMS resin can be easily molded and has a high surface activation level.

Next, a measuring method with a cellular electrophysiology sensor, an example of measuring device 1001 in accordance with the embodiment will be described.

As shown in FIG. 4, a pipettor is inserted into inlet 13 (see FIG. 1) to inject liquid 916 to entirely fill the cavity. Liquid 916 is extracellular solution that is electrolytic solution. Next, pipettors are inserted to communication openings 15A to 15F to inject liquids 919A to 919F to entirely fill cavities 19A to 19F. Liquids 919A to 919F are intracellular solution that is electrolytic solution.

The extracellular solution, such as liquid 916, obtained from, e.g. a mammalian muscle cell, is typically electrolytic solution containing about 4 mM of $K^+$ ions, about 145 mM of $Na^+$ ions, and 123 mM of $Cl^-$ ions. The intracellular solution, such as liquids 919A to 919F, is electrolytic solution containing 155 mM of $K^+$ ions, 12 mM of $Na^+$ ions, and 4.2 mM of $Cl^-$ ions. Liquids 916 and 919A to 919F have an optimal chemical composition that is appropriately changed depending on the measuring target or purpose.

Figure 5:
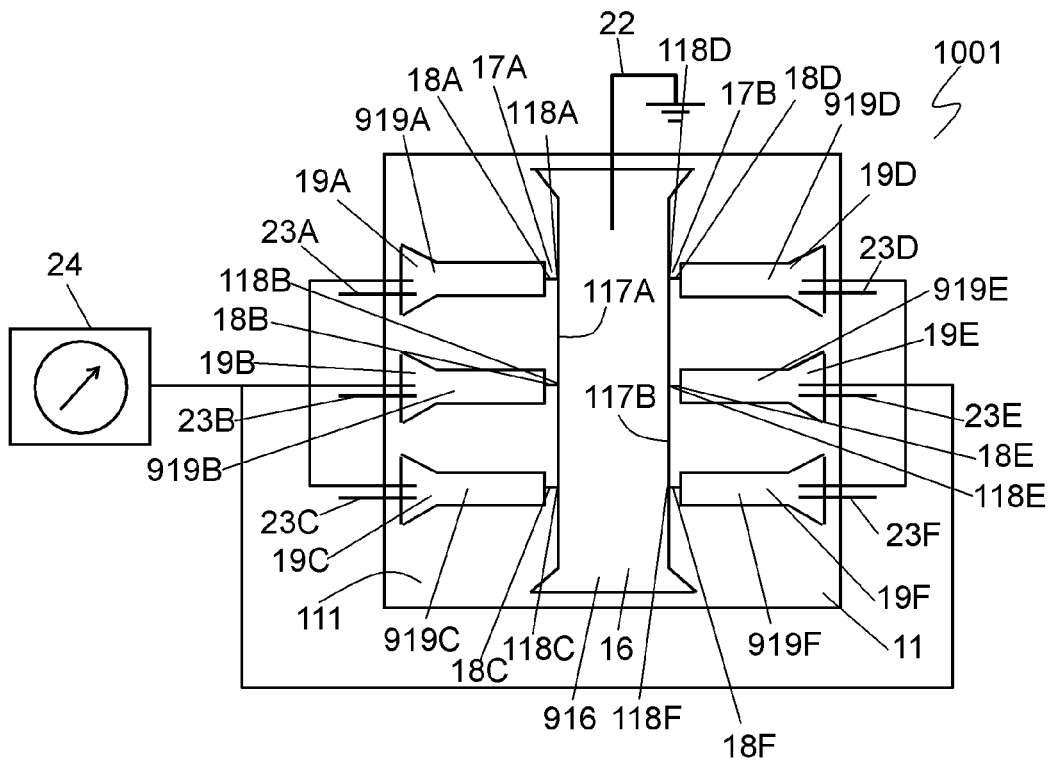
FIG. 5 is a schematic view of the measuring device for illustrating an operation of the device in accordance with the embodiment.
Figure 6A:
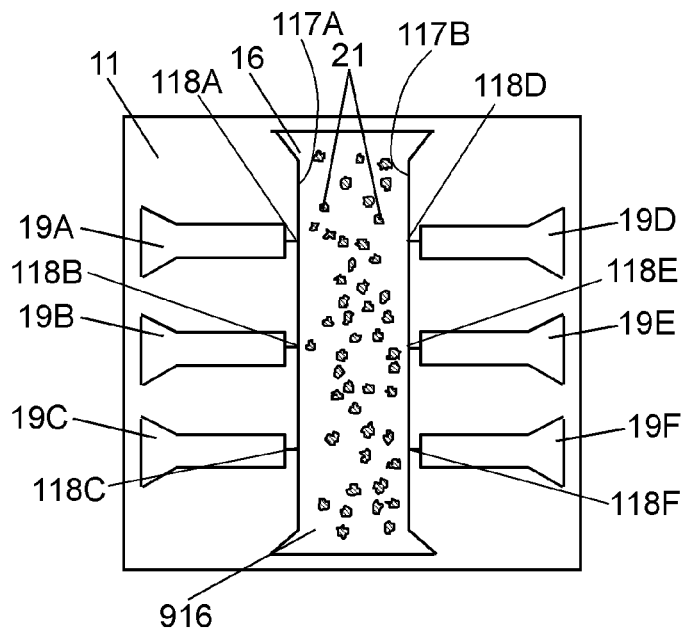
FIG. 6A is a top view of the measuring device in accordance with the embodiment for illustrating an operation of the device.
Figure 6B:
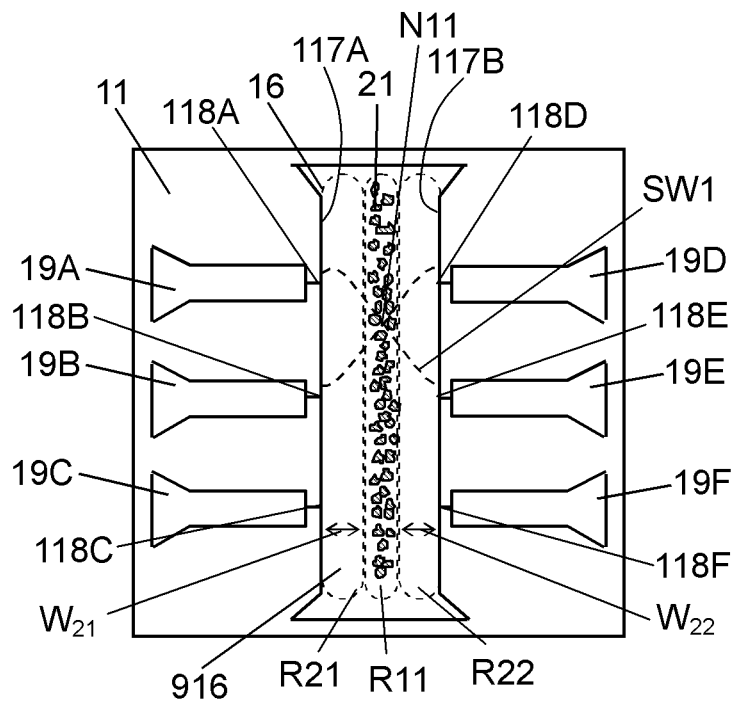
FIG. 6B is a top view of the substrate of the measuring device in accordance with the embodiment for illustrating an operation of the device.
Figure 6C:
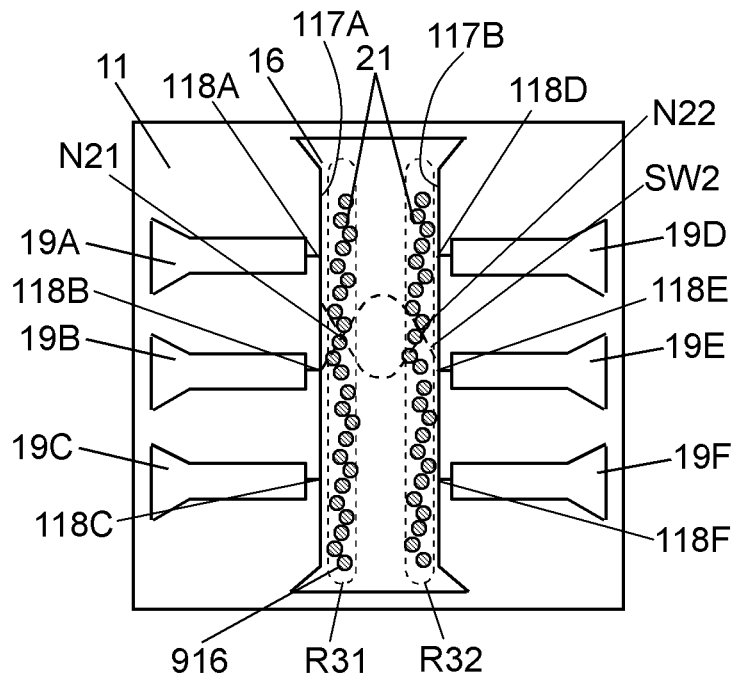
FIG. 6C is a top view of the substrate of the measuring device in accordance with the embodiment for illustrating an operation of the device.

FIG. 5 is a schematic view of measuring device 1001 for illustrating an operation of the device. FIGS. 6A to 6C are a top view of substrate 11 for illustrating the operation of measuring device 1001. After cavities 16 and 19A to 19F are filled with liquids 916 and 919A to 919F, respectively, reference electrode 22 is inserted to inlet 13 or outlet 14, as shown in FIG. 5, to cause liquid 916 to contact reference electrode 22. Measuring electrodes 23A to 23F are inserted to communication openings 15A to 15F, and contact liquids 919A to 919F, respectively. Liquids 919A to 919F are intracellular solution. Cavities 19A to 19F are connected to suction apparatus 24. Liquid 916 that is extracellular solution and liquids 919A to 919F that are intracellular solutions enter through-holes 18A to 18F, thereby forming an electrical circuit between reference electrode 22 and each of measuring electrodes 23A to 23F. As a result, a conduction resistance value of about 100 kΩ to 20MΩ is observed between reference electrode 22 electrically connected to liquid 916 of extracellular solution and each of measuring electrodes 23A to 23F electrically connected to liquids 919A to 919F of intracellular solution.

Next, as shown in FIG. 6A, test object 21 suspended in liquid 916 of extracellular solution is input from inlet 13 via a pipettor.

Then, when vibration generator 20 vibrates at a predetermined frequency, the vibration transmits to cavity 16. As shown in FIG. 6B, standing wave SW1 is generated between side surfaces 117A and 117B in cavity 16. Standing wave SW1 is a fundamental wave that generates only one node N11 between side surfaces 117A and 117B. When standing wave SW1 is generated, test objects 21, solid components, concentrate in region R11 in which node N1 of standing wave SW1 is generated. As a result, the anti-node of standing wave SW1 between node N11 of standing wave SW1 and each of opening sections 118A to 118F produces regions R21 and R22 that do not include test objects 21 and that extend along side surfaces 117A and 117B, respectively. Width $W_{21}$ of region R21 perpendicular to side surface 117A (117B) is a distance from each of opening sections 118A to 118C to region R11 in which test objects 21 concentrate. Similarly, width $W_{22}$ of region R22 perpendicular to side surface 117A (117B) is a distance from each of opening sections 118D to 118F to region R11.

Next, insides of cavities 19A to 19F are decompressed with common suction apparatus 24 via pressure transmission tubes. As a result, test objects 21 are attracted toward opening sections 118A to 118F provided in side surfaces 117A and 117B of partition wall sections 17A and 17B constituting the side surface of cavity 16. Then, test objects 21 are captured at opening sections 118A to 118F. Widths $W_{21}$ and $W_{22}$ of regions R21 and R22 are preferably not less than 30 μm. In the case that widths $W_{21}$ and $W_{22}$ are excessively small and test objects 21 exist at positions excessively close to opening sections 118A to 118F, test objects 21 are sucked and move at an insufficient speed, even when the suction is started through through-holes 18A to 18F. This consequently causes test objects 21 to adhere to opening sections 118A to 118F at an insufficient pressure when test objects 21 contact opening sections 118A to 118F. This prevents test objects 21 from adhering to opening sections 118A to 118F, thus failing to form the giga-seal. Once test object 21 has the giga-seal failed, even if the test object 21 is sucked at a large suction force, the pressure at which test object 21 adheres to opening sections 118A to 118F cannot be increased. Thus, a giga-seal status cannot be formed, thus resulting in a failed measuring. The fact that the measuring failure as described above is often caused is clear from a patch clamp apparatus that is this type of conventional measuring apparatus. Thus, regions R21 and R22 in which test object 21 does not exist are formed so that the suction is started from an appropriate distance that is preferably not less than 30 μm.

As described above, test objects 21 captured at opening sections 118A to 118E are always sucked from region R11 whenever the measurement is carried out. Thus, the speed is fixed at every capture and the impact received by test objects 21 is stable whenever the measurement is carried out.

When the vibration is generated by vibration generator 20 at a doubled predetermined frequency, standing wave SW2 having two nodes N21 and N22 is generated, as shown in FIG. 6C. Test objects 21 concentrate in two regions R31 and R32 in which two nodes N21 and N22 are generated, respectively. In this case, test objects 21 can concentrate at positions closer to opening sections 118A to 118F than standing wave SW1 that is a fundamental wave shown in FIG. 6B. This can consequently allow test objects 21 to be sucked and captured at opening sections 118A to 118F even when the suction force from cavities 19A to 19F is small.

When the vibration is generated by vibration generator 20 at a frequency multiplied by an integral, such as three or four, test objects 21 can concentrate at positions closer to opening sections 118A to 118F. However, this case also requires a region not having therein test object 21 existing therein to have an appropriate width along side surfaces 117A and 117B having opening sections 118A to 118F. For example, in the case that cavity 16 having width $W_{16}$ of 200 μm between side surfaces 117A and 117B vibrates at a frequency which is a double of the fundamental wave frequency of 3.5 MHz, two regions in which test cells 21 do not concentrate are produced between the region in which test objects 21 concentrate and each of side surfaces 117A and 117B. These two regions extend in parallel to side surfaces 117A and 117B. In this case, test objects 21 concentrate in a region away from side surfaces 117A and 117B of cavity 16 by a distance of 50 μm. This distance sufficiently prevents test objects 21 from contacting opening sections 118A to 118F of through-holes 18A to 18F in the case that test object 21 is a cell generally having a diameter ranging from 10 μm to 20 μm.

When test objects 21 are sucked at an excessively-large suction force, test objects 21 may brake, depending on the type of test object 21, due to the impact caused by capturing test objects 21 at opening sections 118A to 118F. In order to avoid this breaking, a region in which test objects 21 concentrate and are suspended is determined prior to the suction, such that test objects 21 in the region can endure such an impact.

When the measurement is stable as described above, test objects 21 are stably absorbed at opening sections 118A to 118F of through-holes 18A to 18F with a high adhesion force at each of plural measurements. Thus, a very-high giga-seal can be obtained with a high probability in which an electrical resistance more than 1 GΩ is established between liquid 916 (extracellular solution) and each of liquids 919A to 919F (intracellular solution).

In the giga-seal, the electrophysiological activity of test objects 21 can be used to accurately measure, with reduced noise, the potential change or current flow of the inside and outside of the cell. Thus, stable measurement can be achieved without wasting every measurement.

In the giga-seal, chemical solution is injected through inlet 13 into cavity 16 via a pipettor to stimulate test object 21. A method of stimulating test object 21 may include, in addition to a method of applying chemical stimulation (e.g., chemical solution) to test object 21, a method of applying physical stimulation such as a an electric signal applied between reference electrode 22 and each of measuring electrodes 23A to 23F. When the chemical or physical stimulation causes test object 21 to have a physicochemical reaction, then the reaction can be detected by a potential difference (or a current value change or a resistance value change) between reference electrode 22 and each of measuring electrodes 23A to 23F.

Different solutions can flow through two inlets 13, respectively, so that the different solutions can flow along side surfaces 117A and 117B of cavity 16, respectively. This can consequently provide, depending on the different solutions, a different reaction of test objects 21 captured at opening sections 118A to 118C and a different reaction of test objects 21 captured at opening sections 118D to 118F. A physicochemical reaction to different solutions shown by test objects 21 can be detected by a potential difference (or a current value change or a resistance value change) between reference electrode 22 and each of measuring electrodes 23A to 23F.

The number of inlets 13 and outlets 14 are not necessarily a plural number and also may be a singular number.

Although through-holes 18A to 18F in side surfaces 117A and 117B of cavity 16 face each other, through-holes 18A to 18F may be provided in only one of side surfaces 117A and 117B.

Measuring device 1001 in accordance with the embodiment can provide improved measurement stability. The standing wave generated by vibration generator 20 allows test objects 21 to be always suspended in the fixed region. Thus, test objects 21 are sucked and captured at opening sections 118A to 118F. Thus, test objects 21 are prevented from being positioned at positions excessively close to through-holes 18A to 18F. In conventional measuring device 501 shown in FIG. 8, cells 8 as test objects are sucked and captured at different distances for every measurement depending on differences of the positions at which cells 8 are firstly input to cavity 2. In measuring device 1001 in accordance with the embodiment, test objects 21 can be captured at opening sections 118A to 118F while contacting side surfaces 117A and 117B at a constant speed, thus maintaining the magnitude of the impact applied from side surfaces 117A and 117B to test object 21. Therefore, test objects 21 can be captured, a giga-seal can be easily established, and a high stable measurement success rate can be achieved.

Furthermore, in measuring device 1001 in accordance with the embodiment, prior to the suction and adhesion of test objects 21 toward through-holes 18A to 18F, test objects 21 are once arranged at a position having a fixed and appropriate distance from opening sections 118A to 118F. By allowing test objects 21 to be sucked and adhered from the appropriate distance, the contact rate during suction can be controlled and the adhesion rate to opening sections 118A to 118F can be improved. The appropriate distance is desirably more than 1.5 times of the diameter of the test object.

Furthermore, in measuring device 1001 in accordance with the embodiment, opening sections 118A to 118F are provided such that test objects 21 captured at opening sections 118A to 118F is prevented from contacting bottom surface 116 and upper surface 216 of cavity 16. When test object 21 is a cell, for example, test objects 21 are generally suspended in liquid 916 that is extracellular solution. Suspended test objects 21 exist, at a high density, at the center of cavity 16 away from side surfaces 117A and 117B of cavity 16. Thus, suspended test objects 21 can be easily captured since opening sections 118A to 118F are located at positions that is higher than bottom surface 116 of cavity 16 and that is lower than upper surface 216. Furthermore, test objects 21 can be captured without contacting bottom surface 116 or upper surface 216 by positioning opening sections 118A to 118F away from bottom surface 116 and upper surface 216 by a distance larger than the diameter of test objects 21.

In measuring device 1001 in accordance with the embodiment, substrate 12 can be made of PDMS resin that is light-transmissive resin. In this case, it is determined visually whether or not dust other than test object 21 is captured at opening sections 118A to 118F. In the case that test object 21 is a cell, for example, test objects 21 can be labeled by fluorescence agent in advance to visually determine easier whether or not dust other than test object 21 is captured at opening sections 118A to 118F.

In measuring device 1001 in accordance with the embodiment, cavities 19A to 19F are independent to each other and measuring electrodes 23A to 23F are also independent to each other. This configuration can separate a measuring electrode connected to an opening section blocked by dust other than test object 21 from a measuring electrode connected to an opening section appropriately blocked by test object 21. Thus, even when an opening section blocked by dust exists, the reaction of test object 21 can be favorably measured efficiently and accurately. As described above, one cavity 16 communicates with cavities 19A to 19F via through-holes 18A to 18F. This structure allows the measuring device to measure the reaction of only the measuring electrode of the cavity of cavities 19A to 19F that is appropriately blocked by test object 21 in the giga-seal. This structure prevents the measuring device from measuring e reaction of the measuring electrode of the cavity connected to a through-hole which is not appropriately blocked at test object 21. Thus, even when some of through-holes 18A to 18F are blocked by dust, the reaction of test object 21 can be measured without having to performing the second suction of test object 21. Thus, measuring device 1001 can efficiently measure the reaction of test object 21.

Figure 7A:
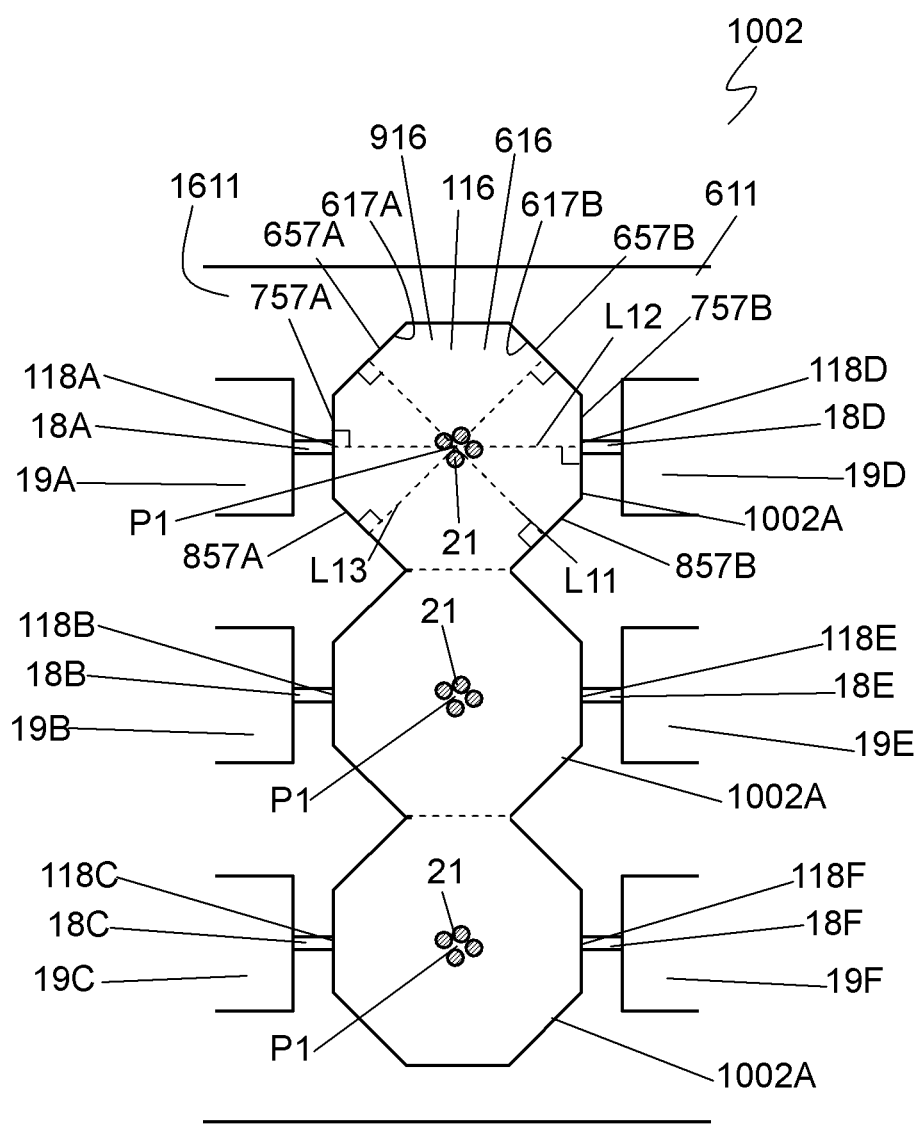
FIG. 7A is a top view of a substrate of another measuring device in accordance with the embodiment.

FIG. 7A is a top view of substrate 611 of another measuring device 1002 in accordance with the embodiment. In FIG. 7A, components identical to those of measuring device 1001 shown in FIG. 6B are denoted by the same reference numerals. Measuring device 1002 includes substrate 611 having upper surface 1611 instead of substrate 11 of measuring device 1001 shown in FIG. 6B. Upper surface 1611 of substrate 611 have cavity 616 therein instead of cavity 16 of measuring device 1001 shown in FIG. 6B. Cavity 616 has side surfaces 617A and 617B facing each other across cavity 616. Opening sections 118A to 118C of through-holes 18A to 18C open to side surface 617A. Opening sections 118D to 118F of through-holes 18D to 18F open to side surface 617B. In measuring device 1001 shown in FIG. 6B, side surfaces 117A and 117B of cavity 16 are single flat surfaces parallel to each other. In measuring device 1002 shown in FIG. 7A, side surface 617A has flat portions 657A, 757A, and 857A which are flat. Side surface 617B has flat portions 657B, 757B, and 857B which are flat. Flat portions 657A and 857B are parallel to each other. Flat portions 757A and 757B are parallel to each other. Flat portions 857A and 657B are parallel to each other. Straight line L11 extending from flat portion 657A to flat portion 857B crosses flat portions 657A and 857B perpendicularly. Straight line L12 extending from flat portion 757A to flat portion 757B crosses flat portions 757A and 757B perpendicularly. Straight line L13 extending from flat portion 857A to flat portion 657B crosses flat portions 857A and 657B perpendicularly. Straight lines L11, L12, and L13 cross at one point P1 that is the midpoint of each of straight lines L11, L12, and L13. The length of straight line L11 that is a distance between flat portions 657A and 857B, the length of straight line L12 that is a distance between flat portions 757A and 757B, and the length of straight line L13 that is a distance between flat portions 857A and 657B are equal to each other.

In measuring device 1002, flat portions 657A, 657B, 757A, 757B, 857A, and 857B constitute plural sides of polygon 1002A in view from bottom surface 116. Polygon 1002A is a regular polygon consisting of an even number of sides (eight sides).

An operation of measuring device 1002 will be described below. When vibration generator 20 (see FIG. 4) vibrates substrate 611 at an appropriate frequency, a wave propagates through liquid 916 filling cavity 616. Plural pairs of flat portions facing each other have an equal distance between the flat portions. Therefore, a standing wave is generated between flat portions 657A and 857B, a standing wave is generated between flat portions 757A and 757B, and a standing wave is generated between flat portions 857A and 657B. These standing waves are superposed to generate a node at point P1. As a result, test objects 21 suspended in liquid 916 concentrate at point P1 at which the node is generated. Opening sections 118A and 118D of through-holes 18A and 18D open at positions at which straight line L12 crosses flat portions 757A and 757B. Measuring device 1002 allows test objects 21 to concentrate in a narrower region than measuring device 1001 shown in FIG. 6B. Thus, test objects 21 more efficiently contact opening sections 118A and 118D at a fixed speed and can be stably captured at opening sections 118A and 118D. Similarly, test objects 21 more efficiently contact opening sections 118B, 118C, 118E, and 118F at a fixed speed and can be stably captured at opening sections 118B, 118C, 118E, and 118F.

Figure 7B:
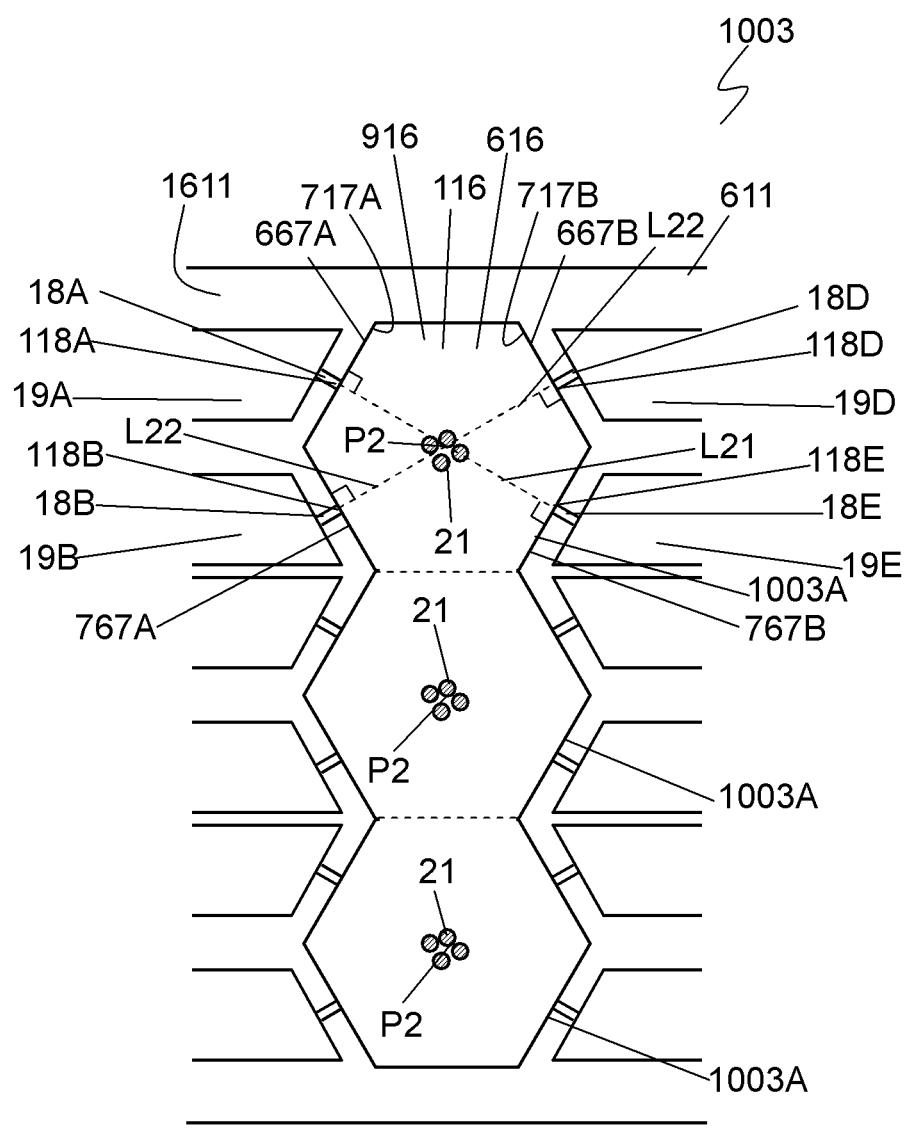
FIG. 7B is a top view of a substrate of still another measuring device in accordance with the embodiment.

FIG. 7B is a top view of substrate 611 of still another measuring device 1003 in accordance with the embodiment. In FIG. 7B, components identical to those of measuring device 1002 shown in FIG. 7A are denoted by the same reference numerals. Cavity 616 provided in upper surface 1611 of substrate 611 of measuring device 1003 shown in FIG. 7B has side surfaces 717A and 717B facing each other across cavity 616. Opening sections 118A and 118B of through-holes 18A and 18B open side surface 717A. Opening sections 118D and 118E of through-holes 18D and 18E open to side surface 717B. In measuring device 1003 shown in FIG. 7B, side surface 717A has flat portions 667A and 767A which are flat. Side surface 717B has flat portions 667B and 767B which are flat. Flat portions 667A and 767B are parallel to each other. Flat portions 767A and 667B are parallel to each other. Straight line L21 extending from flat portion 667A to flat portion 767B crosses flat portions 667A and 767B perpendicularly. Straight line L22 extending from flat portion 767A to flat portion 667B crosses flat portions 767A and 667B perpendicularly. Straight lines L21 and L22 cross each other at point P2 that is the midpoint of each of straight lines L21 and L22. The length of straight line L21 that is a distance between flat portions 667A and 767B is equal to the length of straight line L22 that is a distance between flat portions 767A and 667B.

In measuring device 1003, flat portions 667A, 667B, 767A, and 767B constitute plural sides of polygon 1003A in view from bottom surface 116. Polygon 1003A is a regular polygon consisting of an even number sides (six sides).

An operation of measuring device 1003 will be described below. When vibration generator 20 (see FIG. 4) vibrates substrate 611 at an appropriate frequency, a wave propagates through liquid 916 filling cavity 616. Plural pairs of flat portions facing each other have an equal distance between the flat portions. A standing wave is generated between flat portions 667A and 767B. A standing wave is generated between flat portions 767A and 667B. These standing waves are superposed to generate a node at point P2. As a result, test objects 21 suspended in liquid 916 concentrate at point P2 at which the node is generated. Opening sections 118A and 118E of through-holes 18A and 18E open at positions at which straight line L21 crosses flat portions 667A and 767B, respectively. Opening sections 118B and 118D of through-holes 18B and 18D open at positions at which straight line L22 crosses flat portions 767A and 667B, respectively. Measuring device 1003 allows test objects 21 to concentrate in a narrower region than measuring device 1001 shown in FIG. 6B. Thus, test objects 21 can be more efficiently captured at opening sections 118A, 118B, 118D, and 118E at a fixed speed.

As shown in FIG. 7B, side surfaces 717A and 717B of cavity 616 of measuring device 1003 has plural flat portions constituting the sides of polygons 1003A that are three regular hexagons. In the above description, opening sections 118A, 118B, 118D, ad 118E open flat portions 667A, 667B, 767A, and 767B constituting plural sides of one polygon 1003A in view from bottom surface 116. Cavities 19A, 19B, 19D, and 19E communicate with cavity 616 via through-holes 18A, 18B, 18D, and 18E, respectively. Similarly, the opening sections of plural through-holes open to plural flat portions constituting plural sides of the other two polygons 1003A in view from bottom surface 116. The plural cavities communicate with cavity 616 via plural through-holes, respectively.

Figure 7C:
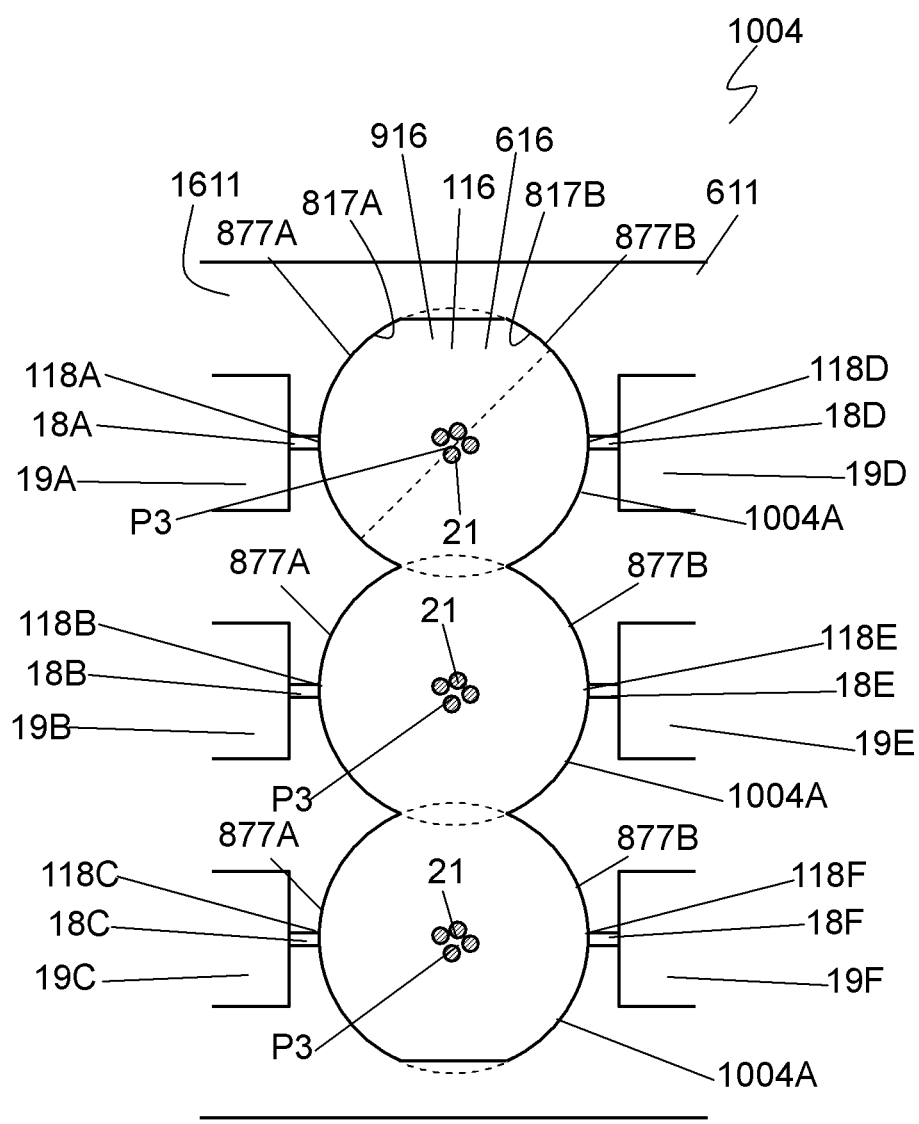
FIG. 7C is a top view of a substrate of a further measuring device in accordance with the embodiment.

FIG. 7C is a top view of substrate 611 of further measuring device 1004 in accordance with the embodiment. In FIG. 7C, components identical to those of measuring device 1002 shown in FIG. 7A are denoted by the same reference numerals. Cavity 616 provided in upper surface 1611 of substrate 611 of measuring device 1004 shown in FIG. 7C has side surfaces 817A and 817B facing each other across cavity 616. Opening sections 118A to 118C of through-holes 18A to 18C open side surface 817A. Opening sections 118D to 118F of through-holes 18D to 18F open to side surface 817B. In measuring device 1004 shown in FIG. 7C, side surface 817A has circularly-arcuate portion 877A having a circularly-arcuate shape in view from bottom surface 116. Side surface 717B has circularly-arcuate portion 877B having a circularly-arcuate shape in view from bottom surface 116. Circularly-arcuate portions 877A and 877B are positioned on circle 1004A in view from bottom surface 116. Circle 1004A has a center at point P3.

An operation of measuring device 1004 will be described below. When vibration generator 20 (see FIG. 4) vibrates substrate 611 at an appropriate frequency, a wave propagates through liquid 916 filling cavity 616. This wave is repeatedly reflected between circularly-arcuate portions 877A and 877B facing each other to generate a standing wave, thereby generating a node at point P3 as the center of circle 1004A. As a result, test objects 21 suspended in liquid 916 concentrate at point P3 at which the node is generated. Opening sections 118A and 118D of through-holes 18A and 18D open to circularly-arcuate portions 877A and 877B, respectively. Measuring device 1004 allows test objects 21 to concentrate in a narrower region than measuring device 1001 shown in FIG. 6B. Thus, test objects 21 can be more efficiently captured at opening sections 118A and 118D at a fixed speed.

In measuring device 1001, width $W_{16}$ of cavity 16 is preferably more than two times of the diameter of test object 21. This configuration prevents test object 21 captured at one of opening sections of opening sections 118A to 118F facing each other from influencing the measuring of other test objects 21 captured at other opening sections.

Opening sections 118A to 118F of through-holes 18A to 18F are preferably arranged at an interval equal to or larger than the diameter of test object 21. This arrangement can provide secure capture of test object 21.

In the case that test object 21 is a cell, a hole is formed in the cell membrane of test object 21 blocking opening sections 118A to 118F to provide test object 21 as a hole cell. In this case, a hole cell can be formed by injecting agent, such as nystatin, through a communication opening of a cavity out of cavities 19A to 19F for which the giga-seal is formed. Alternatively, a hole may be formed in the cell membrane of the cell blocking an opening section connected to a cavity of cavities 19A to 19F for which the giga-seal is formed, by sucking the cell membrane through the cavity.

In FIG. 5, communication openings 15A to 15F communicating with cavities 19A to 19F, respectively, are connected to one common suction apparatus 24. In measuring device 1001 according to the embodiment, plural suction apparatuses may be independently connected to communication openings 15A to 15F, respectively. The plural independent suction apparatuses can suck cavities 19A to 19F independently to one another. However, single common suction apparatus 24 connected to communication openings 15A to 15B can control the suctions of cavities 19A to 19F simultaneously, thus, being desirably used.

As described above, measuring device 1001 is configured to measure the reaction of test objects 21 suspended in liquid 916. Base 51 has cavity 16 configured to store liquid 916 therein and cavities 19A to 19F. Vibration generator 20 generates a standing wave in liquid 916 stored in cavity 16. Base 51 has through-holes 18A to 18F, inlet 13, and communication openings 15A to 15F. Through-holes 18A to 18F allow cavities 19A to 19F to communicate with cavity 16, respectively. Inlet 13 allows cavity 16 to communicate with the exterior of base 51. Communication openings 15A to 15F allow cavities 19A to 19F to communicate with an outside of base 51. Through-holes 18A to 18F have opening sections 118A to 118F, respectively. Opening sections 118A to 118F open to cavity 16 and capture test objects 21.

Inner wall surface 516 of cavity 16 has bottom surface 116, upper surface 216, and side surfaces 117A and 117B having opening sections 118A to 118F therein. Opening sections 118A to 118F are provided at positions at which test objects 21 captured at opening sections 118A to 118F are located away from bottom surface 116 and upper surface 216 of cavity 16. Side surfaces 117A and 117B may be parallel to each other.

Opening sections 118A and 118D face each other across cavity 16. Opening sections 118B and 118E face each other across cavity 16. Opening sections 118C and 118F may face each other across cavity 16.

Vibration generator 20 is operable to generate a standing wave to position test objects 21 in predetermined region R11 in cavity 16. Vibration generator 20 is operable to capture test objects 21 at opening sections 118A to 118F by sucking liquid 916 from cavities 19A to 19F while test objects 21 are positioned in predetermined region R11. Predetermined region R11 is away from opening sections 118A to 118F by a distance more than 1.5 times of the diameters of test objects 21.

Cavities 19A to 19F are configured to store liquids 919A to 919F independently, respectively. Reference electrode 22 is configured to contact liquid 916. Measuring electrodes 23A to 23F are configured to contact liquids 919A to 919F, respectively.

Base 51 includes substrate 11 and substrate 12 joined to upper surface 111 of substrate 11. Upper surface 111 of substrate 11 has cavities 16 and 19A to 19F provided therein. Cavities 16 and 19A to 19F are covered up with substrate 12.

In the embodiment, terms indicating directions, such as "upper surface", "lower surface", and "bottom surface", indicate relative directions depending only on a relative positional relation of components, such as substrates 11 and 12, of measuring device 1001, and do not indicate absolute directions, such as a vertical direction.

INDUSTRIAL APPLICABILITY

A measuring device according to the present invention can stably measure the pharmacological reaction of a test object plural times efficiently.

REFERENCE MARKS IN THE DRAWINGS

11 Substrate (First Substrate)
12 Substrate (Second Substrate)
13 Inlet
15A-15F Communication Opening
16 Cavity (First Cavity)
18A-18F Through-Hole
19A-19F Cavity (Second Cavity)
20 Vibration Generator
21 Test Object 22 Reference Electrode
23A-23F Measuring Electrode
51 Base
118A-118F Opening Section
516 Inner Wall Surface
657A, 757A, 857A Flat Portion (First Flat Portion)
657B, 757B, 857B Flat Portion (Second Flat Portion)
877A Circularly-Arcuate Portion (First Circularly-Arcuate Portion)
877B Circularly-Arcuate Portion (Second Circularly-Arcuate Portion)
916 Liquid (First Liquid)
919A-919F Liquid (Second Liquid)

The invention claimed is:

1. A measuring device for measuring a reaction of a plurality of test objects suspended in a first liquid, said measuring device comprising:
    a base having a first cavity and a plurality of second cavities provided therein, the first cavity being configured to store the first liquid; and
    a vibration generator that generates a standing wave in the first liquid stored in the first cavity,
    wherein the base has a plurality of through-holes, an inlet, and a plurality of communication openings provided therein, each of the plurality of through-holes allowing respective one of the plurality of second cavities to communicate with the first cavity, the inlet allowing the first cavity to communicate with an outside of the base, each of the plurality of communication openings allowing respective one of the plurality of second cavities to communicate with an outside of the base, and
    wherein the plurality of through-holes have a plurality of opening sections, respectively, the plurality of opening sections opening to the first cavity and being configured to capture the plurality of test objects.

2. The measuring device according to claim 1,
    wherein an inner wall surface of the first cavity has a bottom surface, an upper surface, and a side surface, the side surface having the plurality of opening sections of the plurality of through-holes provided therein, and
    wherein the plurality of opening sections of the plurality of through-holes are provided at positions causing the plurality of test objects captured at the plurality of opening sections to be located away from the bottom surface and the upper surface of the first cavity.

3. The measuring device according to claim 1, wherein an inner wall surface of the first cavity has a first side surface and a second side surface facing each other and extending in parallel to each other, the first side surface and the second side surface having the plurality of opening sections of the plurality of through-holes provided therein.

4. The measuring device according to claim 3, wherein the plurality of opening sections of the plurality of through-holes face each other to across the first cavity.

5. The measuring device according to claim 1,
    wherein an inner wall surface of the first cavity has a bottom surface, a first side surface, and a second side surface, the first side surface and the second side surface facing each other and having the plurality of opening sections of the plurality of through-holes provided therein,
    wherein the first side surface has a plurality of first flat portions which are flat,
    wherein the second side surface has a plurality of second flat portions which are flat,
    wherein the plurality of first flat portions and the plurality of second flat portions constitute a plurality of pairs of first flat portions and second flat portions, each of the plurality of pairs of first flat portions and second flat portions including a first flat portion and a second flat portion facing each other, and
    wherein a distance between a first flat portion and a second flat portion of one of the plurality of pairs of the first flat portions and the second flat portions is equal to a first flat portion and a second flat portion any other pair out of pairs of the first flat portions and the second flat portions.

6. The measuring device according to claim 1,
    wherein an inner wall surface of the first cavity has a bottom surface, a first side surface, and a second side surface, the first side surface and the second side surface facing each other and having the plurality of opening sections of the plurality of through-holes provided therein,
    wherein the first side surface has a first circularly-arcuate portion having a circularly-arcuate shape in view from the bottom surface,
    wherein the second side surface has a second circularly-arcuate portion having a circularly-arcuate shape in view from the bottom surface, and
    wherein the first circularly-arcuate portion and the plurality of second circularly-arcuate portions are positioned on a single circle in view from the bottom surface.

7. The measuring device according to claim 1,
    wherein the vibration generator is operable to generate the standing wave to position the plurality of test objects within a predetermined region in the first cavity, and
    wherein the measuring device is operable to capture the plurality of test objects at the plurality of opening sections by sucking the first liquid from the plurality of second cavities while the plurality of test objects is positioned within the predetermined region.

8. The measuring device according to claim 7, wherein the predetermined region is away from the plurality of opening sections of the plurality of through-holes by a distance not smaller than 1.5 times of each of diameters of the plurality of test objects.

9. The measuring device according to claim 1, wherein the plurality of second cavities are configured to store second liquids independently from each other, said measuring device further comprising:
    a reference electrode configured to contact the first liquid; and
    a plurality of measuring electrodes configured to contact the second liquids, respectively.

10. The measuring device according to claim 1,
    wherein the base includes:
        a first substrate; and
        a second substrate joined to an upper surface of the first substrate,
    wherein the first cavity and the second cavity are provided in the upper surface of the first substrate, and
    wherein the first cavity and the second cavity are covered by the second substrate.

* * * * *